United States Patent [19]
Growdon et al.

[11] 4,355,027
[45] Oct. 19, 1982

[54] PROCESS AND COMPOSITION FOR TREATING DISORDERS BY ADMINISTERING PIRACETAM AND CHOLINE

[75] Inventors: John H. Growdon, Brookline; Richard J. Wurtman, Boston, both of Mass.

[73] Assignee: Massachusetts Institute of Technology, Cambridge, Mass.

[21] Appl. No.: 284,768

[22] Filed: Jul. 20, 1981

Related U.S. Application Data

[63] Continuation-in-part of Ser. No. 229,704, Jan. 30, 1981, which is a continuation-in-part of Ser. No. 126,124, Feb. 29, 1980, abandoned, which is a continuation-in-part of Ser. No. 88,227, Oct. 25, 1979, abandoned, which is a continuation of Ser. No. 847,967, Nov. 2, 1977, abandoned.

[51] Int. Cl.³ .................... A61K 31/40; A61K 31/685
[52] U.S. Cl. ..................................... 424/199; 424/274
[58] Field of Search ........................... 424/199; 19/274

[56] References Cited
PUBLICATIONS

New England J. Med., 6-11-81, pp. 1490-1491.

Primary Examiner—Stanley J. Friedman
Attorney, Agent, or Firm—Arthur A. Smith, Jr.; Paul J. Cook

[57] ABSTRACT

Choline or a natural or synthetic compound that dissociates to form choline is administered to a patient concomitantly with piracetam [(oxo-2-pyrrolidinyl-) 2 acetamine] in order to potentiate the effect of the drug by increasing acetylcholine levels in the brain or other tissues, and/or to suppress, or block the development of, unwanted side effects of the drug, by increasing acetylcholine levels in the brain or other tissues.

10 Claims, No Drawings

PROCESS AND COMPOSITION FOR TREATING DISORDERS BY ADMINISTERING PIRACETAM AND CHOLINE

The Government has rights in this invention pursuant to Grant No. MH-28783 from the National Institute of Mental Health.

REFERENCES TO RELATED APPLICATIONS

This application is a continuation-in-part of Ser. No. 229,704, filed Jan. 30, 1981, which in turn is a continuation-in-part of Ser. No. 126,124 filed 2-29-80, now abandoned, which, in turn is a continuation-in-part of Ser. No. 88,227, filed Oct. 25, 1979, now abandoned, which, in turn, is a continuation of Ser. No. 847,967, filed Nov. 2, 1977, now abandoned.

BACKGROUND OF THE INVENTION

This invention relates to a process and composition for the administration of choline, or natural or synthetic compounds that dissociate to form choline, along with piracetam, in order to treat human disorders by increasing actylcholine levels in brain and other tissues.

There are a number of diseases which affect acetylcholine-containing neurons in the brain or other tissues, and which are treated by drugs that cause undesired side effects by diminishing acetylcholine's release; there also exist diseases now treated by other drugs in which the potency and/or efficacy of the drugs could be improved by combining them with choline or natural or synthetic compounds that dissociate to form choline in order thereby to enhance the release of acetylcholine. Such diseases include both those primarily involving the brain (e.g., diseases of higher cortical functions; psychiatric illnesses; movement disorders) and those involving the peripheral nervous system (e.g., neuromuscular disorders). Piracetam [(oxo-2-pryyolidinyl-1)2 acetamine] reported by improved memory and learning ability in normal people and those with memory impairments. Piracetam also appears to deplete brain levels of acetylcholine and therefore impairs acetylcholine's subsequent release. When drugs, including piracetam release too much acetylcholine, they subsequently cease to function as intended and in many instances exacerbate the very adverse physical condition they are intended to treat.

It would be desirable to provide a means for alleviating piracetam's undesirable effect of depleting brain levels of acetylcholine in order to retain its efficacy after administration to a patient.

SUMMARY OF THE INVENTION

This invention is based upon the discovery that choline or a physiologically-acceptable natural or synthetic compound that dissociates to form choline, when administered concomitantly the drug, with piracetam can, by increasing neuronal acetylcholine levels, (1) reduce or prevent undesirable side effects of the drug associated with inadequate acetylcholine release, and/or (2) potentiate the effectiveness of the drug. The choline and drug may be administered orally such as in tablet, capsule or liquid form or parenterally by intravenous, intramuscular or subcutaneous injection. The process of this invention is useful even with patients having a prior history of the undesirable side effect or or sub-optimal therapeutic response, or of therapeutic responses requiring a very large drug dose, but who continue taking the drug.

DETAILED DESCRIPTION OF SPECIFIC EMBODIMENTS

In accordance with this invention, choline or a compound that dissociates to form choline is orally administered to a patient prior to or together with the drug, piracetam, in order to increase blood levels of choline, and thereby to increase the level of acetylcholine in the brain. The acetylcholine is synthesized from choline and acetyl CoA in a reaction catalyzed by choline acethyltransferase (CAT). It has been found that the administration of choline or a compound that dissociates to form choline potentiates the drug by reducing the incidence or suppressing side effects of the drug and/or that lower dosages of the drug are needed to attain the desired effects of the drug. While the results obtained will vary from patient to patient, the reduced side effects and increased efficacy observed are sufficiently significant as to justify the conclusion that their reduction is caused by administration of choline or a compound that dissocates to form choline.

The piracetam can be administered at a dosage now presently employed, i.e., between about 0.1 and 10 g/day and can be administered by the usual route, i.e., oral, or parenteral.

The choline can be administered as choline salts, such as the chloride bitartrate or the like, or as a compound that dissociates to choline, such as an acyglycerophosphocholine, e.g., lecithin, lysolecithin, glycerophosphatidyl choline, mixtures thereof or the like. By the term acylglycerophosphochloine as used herein is meant a compound of the formula:

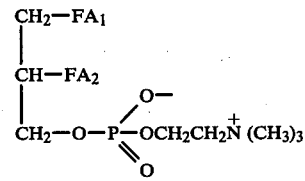

wherein $FA_1$ and $FA_2$ can be the same or different and are fatty acid residues having from 6–26 carbon atoms, usually 16–24 carbon atoms and can be saturated or unsaturated such as palmitic acid, palmitoleic acid, stearic acid, oleic acid, linoleic acid, eicosenoic acid, arachidonic acid, docosahexaenoic acid, eicosapentaenoic acid, linolenic acid, mixtures thereof or the like. The fatty acid residues of the acylglycerophosphocholine can be varied easily by contacting the acylglycerophosphocholine choline, e.g., a lecithin with phospholipase A1 or A2 (to cleave one fatty acid residue) or then phospholipase B (when desired to cleave both fatty acid residues) and then contacting the cleaved compound with the fatty acid of choice. These choline producing compounds also can be administered to patients having lower than normal plasma choline levels, such as patients experiencing renal dialysis. It is preferred to employ an acyglycerophosphocholine, e.g., lecithin as the choline source since it is not degraded in the contrast to choline. The choline or compound that dissociates to choline is administered so that a choline level of at least about 20–30 nanomoles/ml and usually between about 10 and 50 n moles/ml is attained in the patient's bloodstream. For example, when administering choline chloride in the form of capsules or tablets, suitable dosages are from about 1 to 30 g/day, preferably 3-20 g/day taken in divided doses 500 to 1000 mg/cap or tab. When choline chloride is administered in liquid form admixed with a conventional liquid carrier such as a sweetened elixir or the like, from about 1 to 10 grams/15 ml, preferably from about 2 to 5 grams/15 ml can be utilized. When utilizing lecithin in a liquid carrier, it is administered in amounts of between about 0.1 and 50 grams/day. When lecithin is administered in granular form, as a table or in a capsule, it is employed in amounts of between about 0.1 and 100 g/day, usually between about 30 and 50 g/day. Normally, lecithin is not available as a pure compound and is available in admixture with other phospholipids wherein the lecithin comprises about 20-30 weight percent of the mixture.

In the process of this invention, the choline or compound that dissociates to choline is administered prior to or concomitantly with the drug. When administered prior to the drug, the period of time between choline administration and drug administration must be less than when acetylcholine concentration reduction begins to occur in the brain. Generally, the period of time between administrations is less than about 36 hours, preferably less than about 24 hours.

The following example illustrates the present invention and is not intended to limit the same.

EXAMPLE I

In four separate experiments, a total of 55 adult (150 g) male Sprague-Dawley rats ("naive rats") received from the animal supplier within the prior 48 h were housed in pairs and given ad libitum access to food (Charles River Mouse and Rat Chow) and water; they received Piracetam intraperitoneally (30, 100, 300 mg/kg, or its diluent) and were killed by microwave irradiation 30 minutes later. Individual hippocampi were assayed for acetylcholine and for choline (13). In two other experiments, similar rats housed for 7 days in our animal colony ("acclimated rats" received water or Piracetam (100 or 300 mg/kg) and were killed 30 minutes later. Brains were dissected and assayed as with the naive animals.

Piracetam administration caused a significant reduction in hippocampal acetylcholine (Table 1), among naive animals, without significantly modifying choline levels. The reduction was slightly greater and was most significant when the 300 mg/kg dose was used; however in the dosage range tested, no clear dose-relationship was observed. Among animals previously housed in our facility for 7 days, no consistent effect of Piracetam on hippocampal acetylcholine or choline was observed (Table I).

TABLE I

| Effect of Piracetam on Hippocampal Acetylcholine in Naive and Acclimated Rate | | |
|---|---|---|
| Treatment | Naive Rats Acetylcholine (nMoles/g tissue) | Acclimated Rats Acetylcholine (nMoles/g tissue) |
| Vehicle (water) | 23.3 ± 1.24 (17) | 20.2 ± 1.7 (11) |
| 30 mg/kg | 17.2 ± 0.96 (9)* | — |
| 100 mg/kg | 17.0 ± 0.98 (13)* | 25.1 ± 3.7 (10) |
| 300 mg/kg | 15.8 ± 0.83 (16)+ | 19.0 ± 1.8 (10) |

*by Scheffe test differs from vehicle (P < 0.005)
+by Scheffe test differs from vehicle (P < 0.001)

Animals were tested within 48 h of receipt from the supplier (naive rats) or were housed in our colony for one week before testing (acclimated rats). Rats received Piracetam (30, 100 or 300 mg/kg) or water intraperitoneally; 30 minutes later they were sacrificed by focussed microwave irradiation, and their hippocampi were analyzed for acetylcholine and choline. Four separate experiments were performed on acclimated rats. Data were pooled and expressed as means±SEM. The total number of anumals in each experimental group is given in parentheses. Brain choline levels in naive and acclimated animals tended to be slightly higher after Piracetam administration (i.e., 49.2±4.44 vs. 66.3±11.76 nMoles/g among accliumated rats); however, these differences were not statistically significant.

No overt behavioral differences were noted between animals receiving or not receiving Piracetam; however this was not examined systematically, and the Piracetam doses used in our study have been reported to facilitate acquisition in a variety of animal learning paradigms.

A reduction in regional brain acetylcholine levels could reflect either slowed synthesis or accelerated release of the transmitter. That Piracetam acted by accelerating acetylcholine's release is suggested by its failure to reduce hippocampal choline levels. The hypothesized increase in acetylcholine release could be associated with increased or decreased hippocampal cholinergic transmission; acetylcholine turnover would be increased but transmission decreased, for example, if Piracetam blocked cholinergic brain receptors. Such as effect has never been demonstrated for this drug, but it cannot be ruled out by present data. If Piracetam actually facilitates hippocampal cholinergic neurotransmission, and if this neurochemical effect is related to its reported action on memory, then it might be possible to amplify its utility by administering it along with choline or lecithin which enhance acetylcholine's synthesis in, and release from, rapidly-firing cholinergic neurons.

We claim:

1. The process of reducing or eliminating undesirable effects of piractam administered to a human which side effects result from inadequate release of brain acetylcholine, which comprises administering concomitantly with the piracetam an amount of a compound effective to raise the bloodstream choline level of a patient to between 10 and 15 nanomoles/ml and to release adequate amounts of brain acetylcholine selected from the group consisting of choline, a salt of choline, lysolecithin, an acyglycerophosphocholine, having the formula:

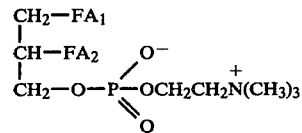

wherein $FA_1$ and $FA_2$ can be the same or different and are fatty acid residues having from 6-26 carbon atoms, glycerophosphatidyl choline and mixtures thereof.

2. The process of claim 1 wherein the piracetam and the compound are administered together as a capsule or tablet.

3. The process of claim 1 wherein the piracetam and the compound are administered together in a liquid.

4. The process of claim 1 wherein the compound is an acyglycerophosphocholine.

5. The process of claim 4 wherein the acyglycerophosphocholine is lecithin.

6. The process of claim 1 wherein the compound is choline chloride.

7. A composition of matter comprising (a) piracetam in an amount of between about 0.1 and 10 g/day which when administered to a human causes side effects associated with inadequate release of brain acetylcholine and (b) an amount of a compound effective to raise the bloodstream choline level of a patient to between about 10 and 15 nanomoles/ml and to release adequate amounts of brain acetylcholine selected from the group consisting of choline, a salt of choline, lysolecithin and acyglycerophosphocholine having the formula:

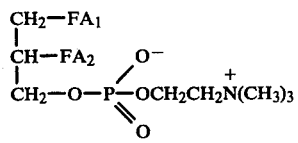

wherein $FA_1$ and $FA_2$ can be the same or different and are fatty acid residues having from 6–26 carbon atoms, glycerophosphatidyl choline and mixtures thereof.

8. The composition of claim 7 wherein the compound is an acyglycerophosphocholine.

9. The composition of claim 8 wherein the acyglycerophosphocholine is lecithin.

10. The composition of claims 7, 8 or 9 wherein the compound is choline chloride.

* * * * *